(12) United States Patent
Mason

(10) Patent No.: US 10,140,674 B2
(45) Date of Patent: Nov. 27, 2018

(54) SYSTEM AND METHOD FOR IMPLEMENTING A DIAGNOSTIC SOFTWARE TOOL

(76) Inventor: Roger Alan Mason, Dumas, AR (US)

(*) Notice: Subject to any disclaimer, the term of this patent is extended or adjusted under 35 U.S.C. 154(b) by 0 days.

(21) Appl. No.: 13/220,953

(22) Filed: Aug. 30, 2011

(65) Prior Publication Data
US 2012/0284298 A1  Nov. 8, 2012

Related U.S. Application Data

(60) Provisional application No. 61/482,683, filed on May 5, 2011.

(51) Int. Cl.
| | | |
|---|---|---|
| G06F 17/30 | (2006.01) |
| G06Q 50/22 | (2018.01) |
| G06Q 50/24 | (2012.01) |
| G06Q 10/06 | (2012.01) |
| G06F 19/00 | (2018.01) |
| G06Q 50/00 | (2012.01) |

(52) U.S. Cl.
CPC ............. *G06Q 50/22* (2013.01); *G06F 19/00* (2013.01); *G06Q 10/06* (2013.01); *G06Q 50/24* (2013.01); *G06F 17/30011* (2013.01); *G06Q 50/01* (2013.01)

(58) Field of Classification Search
CPC ............. G06F 19/321; G06F 17/30011; G06F 17/3028; G06F 17/30525; G06F 19/322; G06F 19/345; G06F 19/363
USPC ....................................................... 707/769
See application file for complete search history.

(56) References Cited

U.S. PATENT DOCUMENTS

| | | | | |
|---|---|---|---|---|
| 5,018,067 A | * | 5/1991 | Mohlenbrock ....... | G06F 19/328 128/920 |
| 7,716,072 B1 | * | 5/2010 | Green, Jr. ............. | G06F 19/328 705/3 |
| 2002/0065682 A1 | | 5/2002 | Goldenberg | |
| 2003/0036683 A1 | * | 2/2003 | Kehr ..................... | G06F 19/325 600/300 |
| 2004/0059714 A1 | * | 3/2004 | Larsen ........... | G06Q 10/063116 |
| 2004/0128165 A1 | * | 7/2004 | Block et al. ...................... 705/2 | |
| 2006/0004605 A1 | * | 1/2006 | Donoghue ............. | G06Q 10/10 705/2 |
| 2006/0111941 A1 | * | 5/2006 | Blom ..................... | G06Q 10/06 705/2 |

(Continued)

*Primary Examiner* — Merilyn P Nguyen
(74) *Attorney, Agent, or Firm* — Liang, Frank & King, LLP; Brian Hennessey

(57) ABSTRACT

Embodiments of the invention are directed toward a computer-implemented interactive diagnostic medical records system operated in conjunction with at least one user device. Interactive processing components provide collaborative interaction between a user and at least one database, the collaboration including deployment of a search module in response to a query associated with the user device, and a diagnostic inquiry module comprising an interactive sequence of at least two linked inquiries transmitted to the user device. In one embodiment, the diagnostic inquiry module is operable to assign a value or "weight" to the user responses to the interactive sequence of at least two linked inquiries. User interface tools may further be associated with the user device for accepting input from the diagnostic inquiry module and correspondingly displaying output as determined by the interactive processing components.

21 Claims, 5 Drawing Sheets

(56) References Cited

U.S. PATENT DOCUMENTS

| | | | |
|---|---|---|---|
| 2007/0106754 A1* | 5/2007 | Moore | G06F 17/3089 709/217 |
| 2007/0162308 A1* | 7/2007 | Peters | G06F 19/322 705/2 |
| 2008/0171916 A1* | 7/2008 | Feder | G06F 19/00 600/300 |
| 2008/0221923 A1* | 9/2008 | Shogan | G06Q 50/22 705/2 |
| 2009/0018862 A1* | 1/2009 | Sanger | G06Q 10/00 705/2 |
| 2009/0240529 A1* | 9/2009 | Chess | G06F 19/328 705/3 |
| 2010/0088120 A1* | 4/2010 | Gonzalvo | G06Q 10/10 705/3 |
| 2011/0040572 A1* | 2/2011 | Chmiel et al. | 705/2 |
| 2011/0054936 A1* | 3/2011 | Cowan | G06Q 10/06 705/3 |
| 2011/0295613 A1* | 12/2011 | Coyne | G06Q 10/10 705/2 |
| 2011/0301441 A1* | 12/2011 | Bandic et al. | 600/306 |
| 2012/0035959 A1* | 2/2012 | Berdia | G06F 19/325 705/3 |

\* cited by examiner

SYSTEM AND METHOD FOR IMPLEMENTING A DIAGNOSTIC SOFTWARE TOOL

PRIORITY

This application claims priority from provisional application Ser. No. 61/482,683, filed on May 5, 2011.

TECHNICAL FIELD OF THE INVENTION

The present invention relates to the operation of health care management system software, and more particularly discloses an interactive software component that allows for an accurate working diagnosis to be made in real-time for each patient under investigation.

BACKGROUND OF THE INVENTION

Physicians typically diagnose a patient's ailment by eliciting a history, or a complete description, of symptoms from the patient. In most situations, the physician will subsequently perform a physical exam guided by the symptom history. Based on information elicited from this investigation, the physician, relying on his knowledge base and experience, reaches a conclusion regarding the most likely diagnosis for the patient, or at least a series of most likely diagnoses (sometimes called a 'differential diagnosis') for that patient. The physician then attempts to narrow this list of differential diagnoses to the most likely working diagnosis using continued clinical observation along with any accompanying diagnostic tests that the physician deems to be necessary. Based on the working diagnosis, the physician then recommends a therapy to treat the identified ailment. For most diagnoses, there are a limited range of recommended treatments proven effective to treat the condition.

Accordingly, the physician's own expertise has always been the limiting factor in reaching an accurate diagnosis. Patients have necessarily become dependent on the unpredictable and variable quality of each physician's clinical ability to reach an accurate diagnosis, typically based on the physician's knowledge base, daily functioning condition and experience—all of which invite at least some amount of human error. Moreover, after diagnosis is reached by the physician, the physician's knowledge and judgment regarding the most effective therapy has always been the sole determinant of which therapeutic options to choose to treat the diagnosed condition.

The practices described above (i.e., taking of a history, physical examinations, testing, etc.) have traditionally been recorded in a hard copy medical record format. However, electronic medical records have more recently become a significant facet of the modern health care system. Electronic maintenance of medical records often ensures the delivery of accurate, cost effective medical care by providing efficient access to a patient's medical history, in addition to a reliable means of recording the patient's present and future complaints. However, while currently available software products proficiently acquire data in a comprehensive, legible, transmissible medical record that primarily facilitates office management and billing efficiencies, these systems are not able to use patient information to serve any type of diagnostic function.

Based on the current state of the art, it would be desirable for medical care professionals to be able to reach consistent and reliable diagnoses that are not limited by the physician's own expertise. This result would be still more desirable in developing nations where there may be a dearth of well qualified physicians, harnessing physician assistants or nurses, able to produce high quality diagnostic results on their own. Thus, it would be advantageous to have an improved method and system for implementing a software tool with interactive diagnostic capabilities, and which uses the artificial intelligence of the system to "weigh" or "judge" the likelihood of a particular diagnosis. It would further be advantageous for this improved method and system to be operable in conjunction with an electronic medical records system.

SUMMARY OF THE INVENTION

Embodiments of the present invention are directed to a computer-implemented interactive system and method that allows a user to use past and/or present information to diagnose a patient. Embodiments of the invention have particular application to use within a hospital or hospital system but may also be applied in other health care institutions as well.

In one aspect of the invention, a computer-implemented interactive system operates in cooperation with a health care institution on behalf of at least one user. The system comprises at least one processor and at least one storage medium adapted to implement: interactive processing components for processing information to provide collaborative interaction over a network between the user and at least one database, the collaboration including deployment of: a search module in response to a query associated with a user device; and a diagnostic inquiry module comprising an interactive sequence of at least two linked inquiries transmitted to the user device, wherein the interactive sequence of at least two linked inquiries is determined at least in part by user input or other previously acquired data; and, user interface tools associated with the user device for accepting input from the diagnostic inquiry module and correspondingly displaying output as determined by the interactive processing components, the user interface tools operable to display and allow the user to respond to the interactive sequence of at least two linked inquiries.

In another aspect of the invention, a computer-implemented interactive method for diagnosing a patient operates in cooperation with a health care institution on behalf of at least one user. The method comprises: processing, by at least one processor in combination with interactive processing components, stored information and user input to provide collaborative interaction between the user and at least one database, the collaborative interaction including deployment of a search module responsive to a query associated with a user device, and a diagnostic inquiry module associated with the at least one database via a network, the diagnostic inquiry module further comprising an interactive sequence of at least two linked inquiries transmitted to the user device, wherein the interactive sequence of at least two linked inquiries is determined at least in part by the user input or other previously acquired data; accepting the user input from the diagnostic inquiry module and correspondingly displaying output on the user device as determined by the interactive processing components; and, displaying an interface on a user device, the diagnosis interface operable to allow the user to respond to the interactive sequence of at least two linked inquiries.

In yet another aspect of the invention a computer-implemented interactive system operates for use in diagnosing a patient. The system comprises: a user device associated with a preloaded module that includes at least one database associated with a catalogue of medical symptoms and conditions; at least one processor and at least one storage medium adapted to implement the following components: interactive processing components for processing information to provide collaborative interaction between a user and the at least one database, the collaboration including deployment of: a search module in response to a query associated with the user device; a diagnostic inquiry module comprising an interactive sequence of at least two linked inquiries transmitted to the user device, wherein the interactive sequence of at least two linked inquiries is determined at least in part by user input or other previously acquired data; and, user interface tools associated with the user device for accepting input from the diagnostic inquiry module and correspondingly displaying output as determined by the interactive processing components, the user interface tools operable to display and allow the user to respond to the interactive sequence of at least two linked inquiries.

DETAILED DESCRIPTION OF THE INVENTIONS

In one embodiment, the present invention allows a user, including an authorized health care professional, to use an interactive software database (and corresponding interface), to suggest a series of possible conditions that most likely explain the patient's illness or other medical condition.

Figure 1:
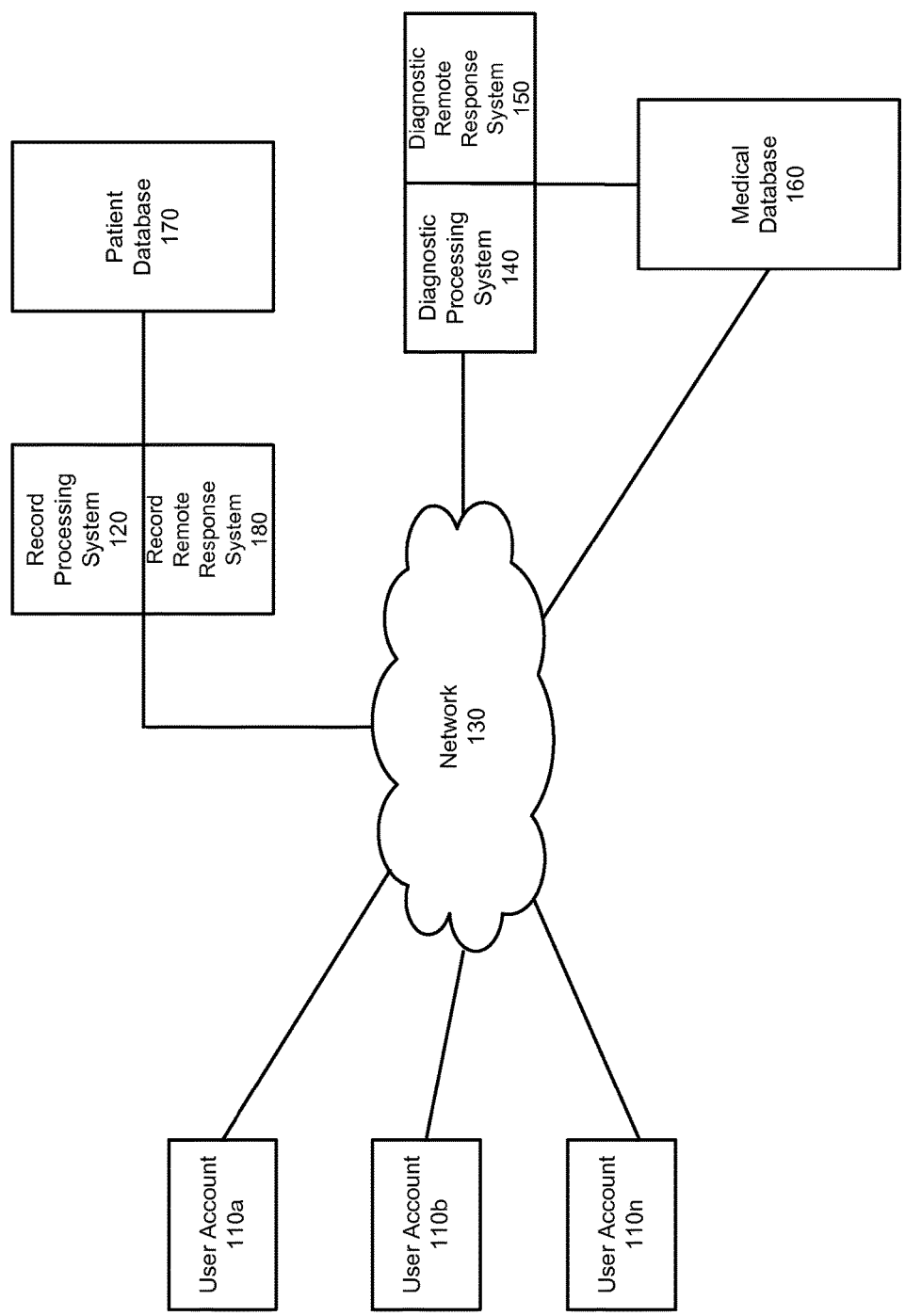
FIG. 1 is a block diagram illustrating an operating environment for a system in accordance with an embodiment of the invention.

FIG. 1 is a block diagram illustrating an operating system environment in accordance with an embodiment of the invention. User accounts 110a . . . 110n may be connected over a network 130 to a diagnostic processing system 140 associated with or including a diagnostic remote response system 150, and a medical database 160. Record processing system 120 associated with or including a record remote response system 180 may additionally be connected to a patient database 170 and further connected to other systems or modules through the network 130. Record processing system 120 may be operable to identify a patient by name, social security number, assigned patient identification number, or through any number of other identifiers (e.g., biometric data, password, etc.).

In this embodiment, the user account holders 110a . . . 110n may have accounts, such as, for example, accounts associated with a treating institution (e.g., hospital, private practice office, other health care institution etc.). The diagnostic processing system 140 associated with the medical database 160 operates in conjunction with a diagnostic remote response system 150 that may be integral with the diagnostic processing system 140. In operation, the user account holders 110a . . . 110n may send a signal to trigger the diagnostic function of the diagnostic processing system 140 by, for example, a user device. The diagnostic remote response system 150 receives the signal and may notify the record processing system 120 of a change in status (i.e., "assessment in progress" or "awaiting examination results") once the diagnostic function is accessed.

The user account holders 110a, 110b . . . 110n may typically be individuals connecting over the network 130 to the diagnostic processing system 140 through the use of computing devices such as desktop, laptop, portable computing devices, or mobile devices, such as a smartphone or tablet device. The user accounts 110a, 110b . . . 110n may hold one or more accounts with the treating institution. The types of accounts may include accounts for physicians, nurses, physician's assistants, nurse practitioners, or other types of accounts. It will be appreciated by those skilled in the art that varying levels of access based on relevant privacy laws (i.e., the Health Insurance Portability and Accountability Act, or "HIPAA") or other preferences may be assigned to the different types of accounts. An account engine may be responsible for generating, maintaining and identifying user accounts and authorizations.

In embodiments of the invention, the diagnostic remote response system 150 and/or diagnostic processing system 140 may provide an interface accessible over the network 130 to display the interface for the diagnostic function of the diagnostic processing system 140, and receive input from the user account holders 110a, 110b . . . 110n. Alternatively, the user account holders 110a, 110b . . . 110n may simply be provided with a phone number or email address associated with the diagnostic remote response system 150 and may send responses to that phone number or email address. In such an embodiment, user account holders 110a, 110b . . . 110n could communicate with the diagnostic processing system via, for example, text messages.

Furthermore, the record remote response system 180 may be in communication with record processing system 120 via the network 130 to convey medical record information about a patient to a user account holder 110a, 110b . . . 110n attempting to access a record. For example, if a user account holder 110a, 110b . . . 110n is attempting to access a record for information on previous testing that has been done on a patient for a specific condition, the record remote response system 180 may notify the record processing system 120 through the institution equipment connected over the network 130. This information can then be considered by the physician while the diagnostic function of the diagnostic processing system 140 is in operation. Those skilled in the art will appreciate that this functionality reduces repetitive testing for the same condition and allows for certain diagnoses to be ruled out immediately.

The record processing system 120 may be adapted to interface with the record remote response system 180. Alternatively, the record remote response system 180 may be integrated with the record processing system 120. The record remote response system 180 provides an account remote control system that enables a user account holder 110a, 110b . . . 110n to remotely access the record processing system 120. In embodiments of the invention, the record remote response system 180 has the capability to receive commands from the user account holders 110a, 110b . . . 110n and execute any queries or commands, and to access records automatically at the direction of the user account holder 110a, 110b . . . 110n without the requirement for manual intervention. The record remote response system 180 may further communicate with the record processing system 120 to enable or disable use of certain functionalities within the record processing system.

The record processing system 120 may further include terminals or other equipment used by the health care industry to maintain and update medical records, and may connect over a network for processing and subsequent access by the user accounts 110*a*, 110*b* . . . 110*n*. The record processing system 120 may also supply information from the patient database 170 for use by the diagnostic processing system 140.

The network 130 is preferably the Internet, but may be or include other types of networks. The network 130 may include a wired or wireless local area network (LAN) and a wide area network (WAN), wireless personal area network (PAN) and other types of networks. When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Some suitable communications protocols may include TCP/IP, UDP, or OSI for example. For wireless communications, communications protocols may include Bluetooth, Zigbee, IrDa or other suitable protocol. Furthermore, components of the system may communicate through a combination of wired or wireless paths.

The diagnostic processing system 140 may be adapted to interface with the diagnostic remote response system 150. Alternatively, the diagnostic remote response system 150 may be integrated with the diagnostic processing system 140. The diagnostic remote response system 150 provides an account remote control system that enables a user account holder 110*a*, 110*b* . . . 110*n* to remotely access the diagnostic processing system 140. In embodiments of the invention, the diagnostic remote response system 150 has the capability to receive commands from the user account holders 110*a*, 110*b* . . . 110*n* and execute any queries or commands at the direction of the user account holder 110*a*, 110*b* . . . 110*n* without the requirement for manual intervention. The diagnostic remote response system 150 may further communicate with the diagnostic processing system 140 to enable or disable use of certain functionalities within the diagnostic processing system 140.

The medical database 160 may be or include any database that stores data relating to the diagnostic function of the diagnostic processing system 140. As set forth above, medical database 160 may typically include information and other data relevant to the operation of the diagnostic function of the diagnostic processing system 140, but may also include other types of data as well; in particular, a searchable data catalogue of symptoms and their associated conditions and/or illnesses. The patient database 170 may typically include information and other data relevant to stored medical records, but may also include other types of patient information as well.

In one embodiment, this invention describes a software model that directs the physician's history acquisition and then based on this history, directs the physician's physical exam so that the most effective physical exam is performed to refine and narrow the differential diagnosis list further to a working diagnosis. This computing environment is described by FIG. 2.

Figure 2:
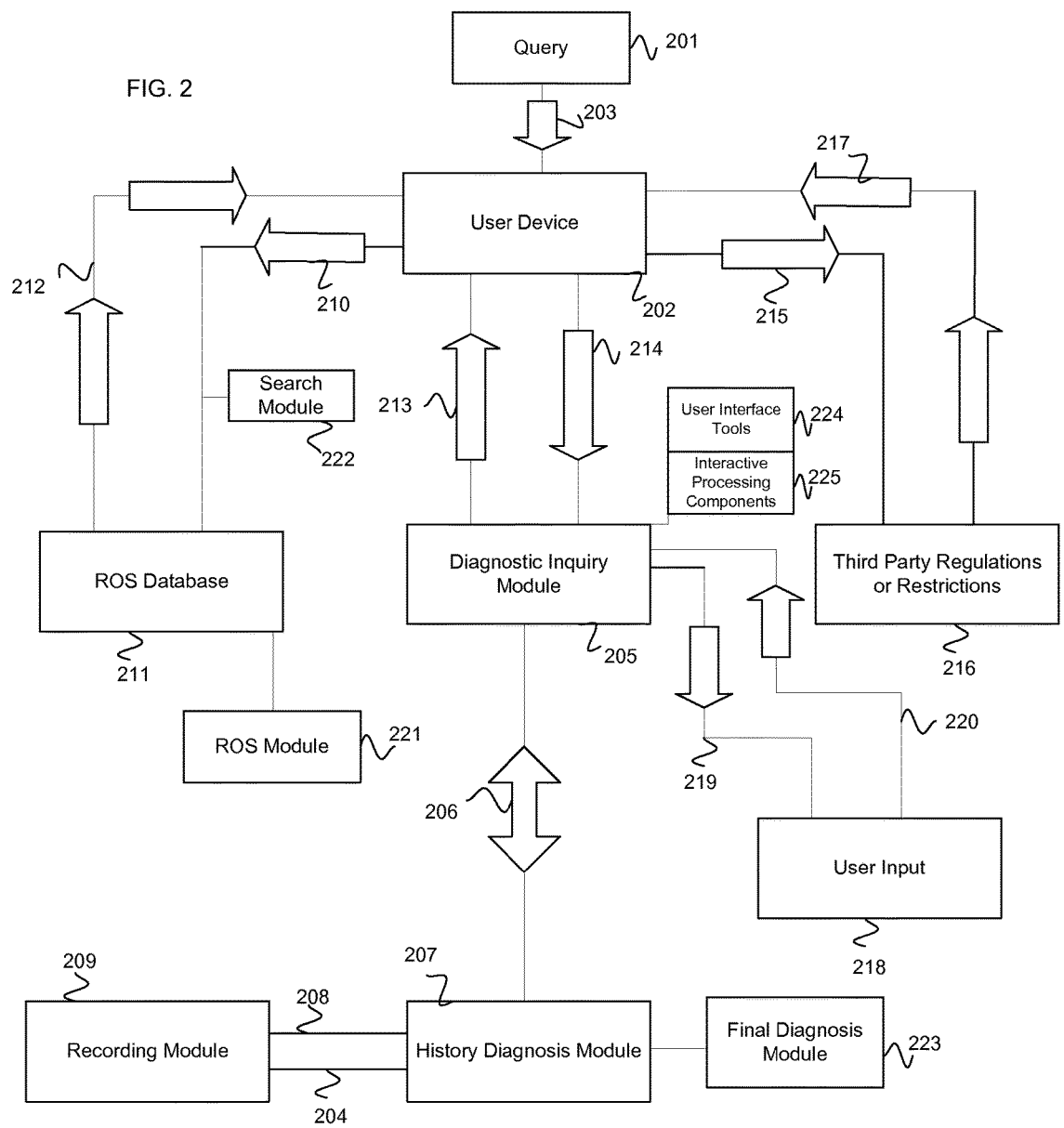
FIG. 2 is a block diagram illustrating a computing environment for implementing a method and system in accordance with an embodiment of the invention.

Referring to FIG. 2, a user may enter a query 201 at a user device 202, the query 201 relating to a patient's symptom(s), sign(s), concern(s), complaint(s), condition(s), or the physician's observations as they relate to the patient's symptom(s), sign(s), concern(s), complaint(s) and condition(s). In various embodiments, the user may be the physician or other appropriate health care professional, the patient, or any combination thereof. In some circumstances, there may be more than one user. With the user's query 201, the user device 202 may then access a search module 222 at 210. The search module 222 is able to access at least one ROS module 221 through a database 211 using a Review of Systems ("ROS") list (or any other standard medical authority and/or searchable catalogue of symptoms). The ROS database 211 may include medical texts or journals, as well as information available on the internet or other network, in order to relate symptoms to each other and direct the query 201 to the appropriate ROS module 221. Those skilled in the art will further appreciate that regular updates to the ROS database 211 may be required. At 212, the ROS module 221 returns a diagnostic inquiry module 205, comprising a list of linked, sequential inquiries, via the user device 202.

Once the appropriate, selected, ROS module 221 transmits a diagnostic inquiry module 205 regarding the patient's symptoms and conditions to the user device 202, the user may enter user input 218 in response, using interactive processing components 225. The ROS module 221 may produce prompts to the user device 202 which may be accessed by the user using user interface tools 224. The prompts may be based on the user's response to the previous inquiry or inquiries. The ROS module 221 may require user input 218, such as "Yes" and "No" responses, and/or responses that may require further evaluation or expertise (i.e., a number input or color description) by the user. Those skilled in the art will appreciate that a user's response to a particular prompt, whether negative or positive, may be given more weight than the user's response to a different prompt, by, for instance, assigning to a user's response a numeric value on a predetermined scale. Those skilled in the art will further appreciate that the system could be implemented with additional hardware that records sounds (for example, heart sounds could be recorded using a microphone-enhanced stethoscope placed on chest wall). Audio sounds assimilated by the computer software could then be analyzed as part of a cardiac auscultory exam. Related technology could be used to assess, for instance, analyzing breath sounds to assess a pulmonary conditions. Each answer may prompt a related question as the ROS module 221 eliminates or attempts to eliminate all possible diagnoses resulting from the search module's 222 search of the ROS database 211. In one possible embodiment, the physician may relate the questions to the patient and answer via a portable tablet with a touch-screen interface.

Once the user has completed the diagnostic inquiry module 205, a list of potential differential diagnoses may be displayed by a history diagnosis module 207 which compiles the responses and organizes them by combining the results of the diagnostic inquiry module 205 with the information in the ROS database 211. In one embodiment, these differential diagnoses may be displayed in order of ascending or descending likelihood of diagnosis.

In one embodiment, the system will be further able to access a patient's previous records to, for example, inform the history diagnosis module 207 that a certain diagnosis has previously been ruled out or to rank the differential diagnoses produced by the history diagnosis module 207 in order of likelihood. In another embodiment, a user such as a physician may wish to simply review a patient's file before meeting with the patient. Information from the patient's record may further refine the pathway to a patient's diagnosis (i.e., if the system is informed that a patient is male at the outset, it will not unnecessarily list 'pregnancy' as a differential diagnosis when the patient complains of stomach pain) and otherwise provide information relevant to the sequential questions to be answered by the user, as well as to any outcomes (i.e., examination methods, treatments, tests, etc.) that may be recommended by the system.

In a further embodiment, the history diagnosis module 207 will also be capable of suggesting a format for any subsequent physical examination that may be necessary. In one embodiment, the history diagnosis module 207 may also provide prompts to the user in order to ensure a proper, thorough exam is accomplished. The prompts may require further user input (i.e., the user may be required to enter information such as temperature, demeanor, heartbeat, etc.) to further narrow the possible range of diagnoses that may exist. Thus, where the user is a physician or other health care professional, the user is able to initiate a limited number of therapeutic options, which may be developed by a national consensus of experts and available as "best practice" recommendations. Similarly, the history diagnosis module 207 may be operable to suggest possible physical examination formats or to suggest further laboratory testing (such as, for instance, blood tests or laparoscopy procedures) that may also assist in the diagnosis of the patient.

Those skilled in the art will further appreciate that additional software could be adapted for use in the operating room. For instance, after suggesting a course of treatment, the system could be configured to give verbal commands describing of the steps of an operation or procedure. Thus, a surgeon would use verbal prompts during the surgical procedure. In a further embodiment, voice recognition software could be used to allow the surgeon to give verbal descriptions of a problem (e.g., "valve blocked"), and the system could respond with options for treatment.

It will also be appreciated by those skilled in the art that a third-party database 216 may contain restrictions or regulations on further tests or procedures that may be performed given the likelihood of a specific diagnosis. Non-limiting examples of rules or regulations that may be stored in the third-party database 216 include applicable Government regulations (such as Medicare or Medicaid), hospital regulations, and insurance procedures. In such an embodiment, the working diagnosis produced allows the history diagnosis module 207 to assign an acuity to the diagnosis of each patient, based on, for example, the severity of the primary condition and affected by any secondary co-morbidities, that allows the payer systems to assign a reasonable and equitable remuneration for quality care defined by computer generated protocols. In one embodiment, the assignment of acuity could be utilized in adoption of certain reimbursement schedules that would compensate physicians or treating institutions for treating severely ill patients. In another embodiment, the third-party database 216 could be used to "alert" the user whether certain procedures or tests are allowed or prohibited by the relevant authority under a patient's particular set of circumstances. Such an embodiment could further allow a physician or health care professional to "override" the regulations or suggested tests or procedures. In some circumstances, the override would require approval from appropriate authorities (for instance, medical authority or authorized insurance representative), available to answer requests on-line immediately through an instant on-line chat capability, or any other communication method.

In another embodiment, a final diagnosis module 223 may further evaluate any examination or testing performed and completed, and rule out earlier diagnoses that may have been incorrect. In another embodiment, the differential diagnoses produced by the history diagnosis module 207, along with the results of any exam or tests, may also be recorded electronically by a recording module 209. The recording module 209 may then record the final output of the history diagnosis module 207 as a final diagnosis using the final diagnosis module 223. In another embodiment, the recording module 209 may further be operable to transmit data regarding some or all of the exchange between various system components and the user (e.g., symptoms, prompts, user responses, differential diagnoses, final diagnoses, applicability of third-party rules, etc.) to a central server. In yet another embodiment, the history diagnosis module 207 and/or final diagnosis module 223 are able to access a separate literature database (not pictured) that is capable of electronically sending the physician descriptive literature on the condition(s) encompassed by the differential diagnoses regarding the possible condition(s) of the patient. Patient-oriented information and other possible user material(s), with educational materials and information on potential therapies, may also be available through this same avenue.

Figure 3:
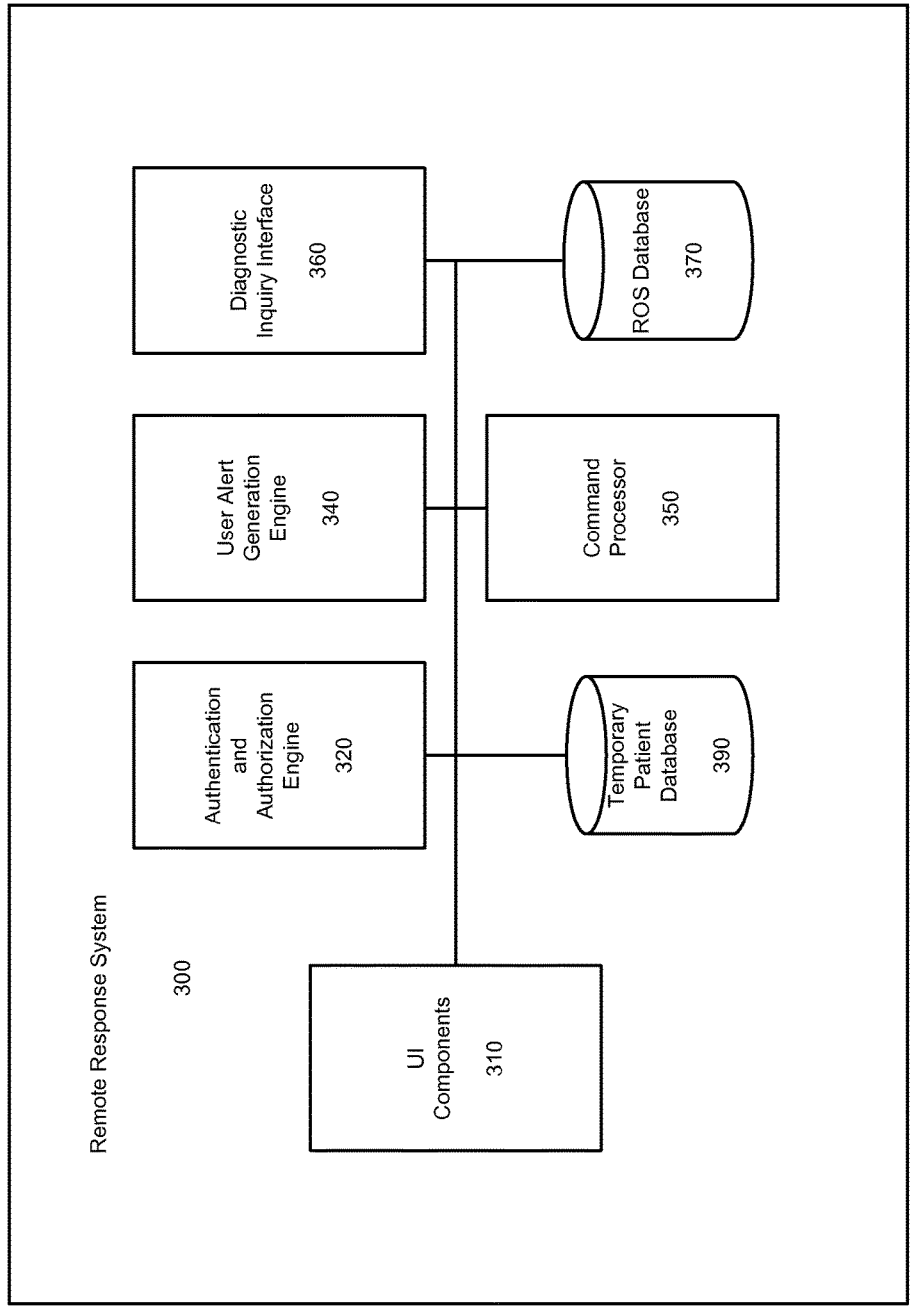
FIG. 3 is block diagram illustrating an embodiment of a remote response system in accordance with an embodiment of the invention.

FIG. 3 is block diagram illustrating an embodiment of a remote response system 300 in accordance with an embodiment of the invention. The remote response system 300 may include, for example, graphical user interface (UI) components 310, an authentication and authorization engine 320, a temporary database for storing accessed patient information 390, a user alert generation engine 340, a command processor 350, a diagnostic inquiry interface 360, and an ROS database 370.

The UI components 310 may be provided by front end components of the remote response system 300. Different user interface configurations may be provided for personal computers and various mobile devices. Mobile devices may be provided with a straightforward ON/OFF command option. Initially, a menu may be provided to enable an account holder to select from a plurality of eligible accounts. This option may be provided, for example via two selectable buttons or a drop down menu.

The authentication and authorization engine 320 may function to authenticate a user and/or a device. For example, the authentication and authorization engine 320 may respond to image capture or biometric data collection in order to authenticate the account holder. The authentication and authorization engine 320 may further check parameters such as, for example, IP address, in order to authenticate the transmitting device. Furthermore, passwords, security questions, and or other security measures may be implemented. In embodiments of the invention, a higher level of security for specific users or specific content would be available.

The user alert generation engine 340 may provide a number of alerts to the user. For example, the user alert generation engine 340 may alert the user to a change in status, to an approved or disapproved treatment option, and/or to a patient's past treatment responses or results. Such alerts may include transactions that are sent between separate user devices (i.e., where one patient requires testing done in both the Cardiology and Oncology departments of a hospital, and the results are recorded separately by two different users). The alert in this instance may be sent in real time upon the command of a user and may notify other users by, for example, via text, email, or push notification.

Furthermore, embodiments of the invention allow for an ON state with respect to some categories of tests, procedures, treatments and the like, and a simultaneous OFF state with respect to others. For example, the account may be ON for a routine preliminary test for Human immunodeficiency virus ("HIV"), but OFF for more unusual or non-standard tests.

The command processor 350 processes commands and/or queries including commands from the users in real time. The command processor 350 operates in response to the commands after authentication and authorization. The command processor 350 may access records in the ROS database 370 to ensure that the command or query is valid and/or otherwise proper. In embodiments of the invention, the command processor 350 may process additional commands such as scheduling commands that provide users with the capability to access or close records at particular points in time. Specific control signals could be implemented for different times or alternatively, users may access an Internet interface to execute scheduling.

Furthermore, the command processor 350 may process commands for setting up recurring appointments. In other words, if a patient visits a hospital, office or other institution regularly (i.e., for an ongoing treatment such as, for instance, dialysis or chemotherapy), and the system is in an ON state, the remote response system may be configured to allow the record to be automatically accessed at that recurring time. This allows the user to efficiently make often routine, but necessary, updates. For a new regular patient, the system may implement a one time "ask" to users before allowing the device to automatically access the patient's records at a recurring time and/or date.

Thus, although the users may issue various types of instructions and/or queries, the functionality for executing the instructions is located within the command processor 350 of the remote response system 300, which in embodiments of the invention is integral with the authenticaton and authorization engine 320. The command processor 350 may be responsive to instructions issued by native applications such as iPhone or iPad applications, Blackberry applications and/or other smartphone applications. The command processor 350 may further be responsive to text messages or could implement a voice recognition unit (VRU) to respond to voice commands. In further embodiments, the remote response system 300 may be responsive to requests received via email, or may implement a website to receive online instructions from account holders.

The diagnostic inquiry interface 360 may communicate with necessary databases such as ROS database 370 in order to submit a proper diagnostic inquiry via the host computer as shown and described in exemplary FIG. 2. As previously described with regards to both FIG. 1 and FIG. 2, the medical ROS database 370 preferably contains user information catalogued from standard Review of Systems ("ROS") list (or any other standard medical authority and/or searchable catalogue of symptoms). In order to interact with this module via the diagnostic inquiry interface 360, the user may, for instance, type a response into a device on a keyboard or tap an option displayed on a touch screen.

The temporary database for storing accessed patient information 390 may be internal or external to the remote response system 300 and may also be accessed by the remote response system 300. The temporary patient database 390 preferably contains user information catalogued a patient's previous medical examinations, tests and/or treatments, and may further include any other information on the patient's medical history, accessed from the permanent patient database as described in FIG. 1. This temporary patient database 390 provides temporary storage while the pathway to a patient's diagnosis and otherwise provides information relevant to the sequential questions to be answered by the user, as well as to any outcomes (i.e., examination methods, treatments, tests, etc.) recommended by the system.

Mobile devices having texting capabilities may not require a particular user interface in order to receive a record request from a user during use in texting mode. Instead, authorized users may merely text a first code to open a patient's record and a second code to close and secure that record. The code to open may, for example, be "OPEN" and the code to close may, for example, be "CLOSE". In order to first open the record, a user may be required to transmit a pre-selected user identifier. Other choices may also be implemented. Additional codes may be used for different types of patients.

In addition to the simple OPEN/CLOSE interfaces, user devices may be equipped with more complex user interfaces that allow scheduling of viewing and closing. For example, a UI calendar may be provided that allows a user to select dates for viewing and closing such as, for instance, according to a patient's appointment schedule. Such an interface may, for example, be provided at an account web site provided by the institution maintaining the electronic records. Even with the texting embodiment, the remote response system 300 may understand various scheduling codes. For example, a code "ON46" may be used to turn leave the record open for six hours or a code "OFFN3" may be used to close and/or file the record in three hours. Leaving a record open may serve as a reminder to a physician who is, for instance, awaiting test results to ensure they are recorded in the electronic file. When the scheduling function is performed as described herein, the remote response system 300 may, in embodiments of the invention, communicate with the user alert generation engine 340 to send a notification to a registered computer or mobile device connected with a user when the account changes status in accordance with a scheduled command. The notification may be a text message, an email, a phone message, or any other type of notification that can appropriately be conveyed to the registered device.

In embodiments of the invention, the UI components 310 may also allow users to configure alerts sent by other users, which may include humans or automated computer alerts, such as for updated test results or specialist examination. Furthermore, in embodiments of the invention, the UI components 310 may provide selectable categories of treatment options and allow users to select an ON status for some tests, treatments and services and an OFF status for others. For example, for a patient that is allergic to penicillin, a user may turn OFF any treatment options that use this medication. Furthermore, the user may be able to specify that the alerts must always remain ON for certain routine tests, treatments, and/or other services.

Additional UI configurations that may be implemented will be understood by those skilled in the art.

Figure 4:
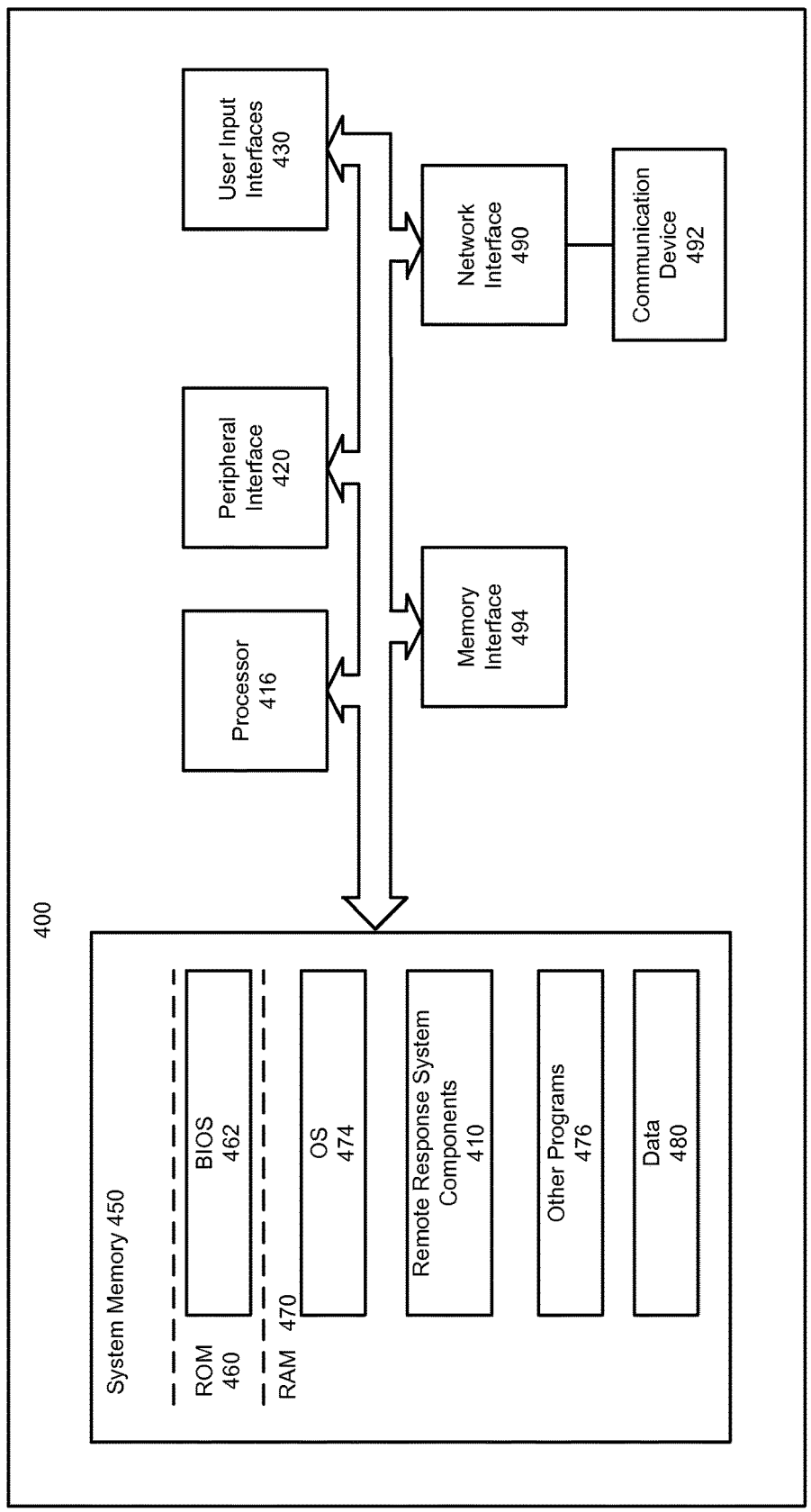
FIG. 4 is a block diagram illustrating a computing environment for implementing a method and system in accordance with an embodiment of the invention.

FIG. 4 is a block diagram illustrating a computing system 400 implementing remote response system applications that may be utilized in accordance with an embodiment of the invention. This configuration is merely exemplary and should not be construed as limiting. It is likely that multiple computing systems or devices will be utilized to implement the method and system in accordance with embodiments of the invention. The computing system 400 may include a processing unit 416, a peripheral interface 420, a user input interface 430, a system bus 440 (not pictured), a system memory 450, a network interface 490, a connected modem, transceiver, adaptor, or other communication device 492, and a memory interface 494. The system bus 440 may be provided for coupling the various system components.

Computers typically include a variety of computer readable media that can form part of the system memory and be read by the processing unit. By way of example, and not limitation, computer readable media may comprise computer storage media and communication media. The system memory 450 may include computer storage media in the form of volatile and/or nonvolatile memory such as read only memory (ROM) 460 and random access memory (RAM) 470.

A basic input/output system (BIOS) 462, containing the basic routines that help to transfer information between elements, such as during start-up, is typically stored in ROM 460. RAM 470 typically contains data and/or program modules that are immediately accessible to and/or presently being operated on by processing unit. The data or program modules may include an operating system 474, remote response system components 410, other program modules 476, and program data 480. The operating system may be or include a variety of operating systems such as Microsoft Windows® operating system, the Unix operating system, the Linux operating system, the Xenix operating system, the IBM AIX™ operating system, the Hewlett Packard UX™ operating system, the Novell Netware™ operating system, the Sun Microsystems Solaris™ operating system, the OS/2™ operating system, the BeOS™ operating system, the Macintosh® operating system, the Apache™ operating system, an OpenStep™ operating system or another operating system of platform.

At a minimum, the memory 450 includes at least one set of instructions that is either permanently or temporarily stored. The processor 416 executes the instructions that are stored in order to process data. The set of instructions may include various instructions that perform a particular task or tasks, such as those shown in the appended flowcharts. Such a set of instructions for performing a particular task may be characterized as a program, software program, software, engine, module, component, mechanism, or tool. The remote response system components 410 may include a plurality of software processing modules stored in a memory as described above and executed on a processor in the manner described herein. The program modules may be in the form of any suitable programming language, which is converted to machine language or object code to allow the processor or processors to read the instructions. That is, written lines of programming code or source code, in a particular programming language, may be converted to machine language using a compiler, assembler, or interpreter. The machine language may be binary coded machine instructions specific to a particular computer. Any suitable programming language may be used in accordance with the various embodiments of the invention. Illustratively, the programming language used may include assembly language, Ada, APL, Basic, C, C++, COBOL, dBase, Forth, FORTRAN, Java, Modula-2, Pascal, Prolog, REXX, and/or JavaScript for example. In embodiments of the invention, Ab Initio™ software is implemented and structured query language (SQL) is implemented for coding.

Further, it is not necessary that a single type of instruction or programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module.

The computing environment may also include other removable/nonremovable, volatile/nonvolatile computer storage media. For example, a hard disk drive may read or write to nonremovable, nonvolatile magnetic media. A magnetic disk drive may read from or write to a removable, nonvolatile magnetic disk, and an optical disk drive may read from or write to a removable, nonvolatile optical disk such as a CD-ROM or other optical media. Other removable/nonremovable, volatile/nonvolatile computer storage media that can be used in the exemplary operating environment include, but are not limited to, magnetic tape cassettes, flash memory cards, digital versatile disks, digital video tape, solid state RAM, and solid state ROM. The storage media are typically connected to the system bus through a removable or non-removable memory interface.

The processing unit 416 that executes commands and instructions may be a general purpose computer, but may utilize any of a wide variety of other technologies including a special purpose computer, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID processor, smart chip, or any other device or arrangement of devices that is capable of implementing the steps of the processes of the invention.

It should be appreciated that the processors and/or memories of the computer system need not be physically in the same location. Each of the processors and each of the memories used by the computer system may be in geographically distinct locations and be connected so as to communicate with each other in any suitable manner. Additionally, it is appreciated that each of the processor and/or memory may be composed of different physical pieces of equipment.

A user may enter commands and information into the computer through a user interface 430 that includes input devices such as a keyboard and pointing device, commonly referred to as a mouse, trackball or touch pad. Other input devices may include a microphone, joystick, game pad, satellite dish, scanner, voice recognition device, keyboard, touch screen, toggle switch, pushbutton, or the like. These and other input devices are often connected to the processing unit through a user input interface that is coupled to the system bus, but may be connected by other interface and bus structures, such as a parallel port, game port or a universal serial bus (USB).

One or more monitors or display devices may also be connected to the system bus via an interface 420. In addition to display devices, computers may also include other peripheral output devices, which may be connected through an output peripheral interface. The computers implementing the invention may operate in a networked environment using logical connections to one or more remote computers, the remote computers typically including many or all of the elements described above.

Various networks may be implemented in accordance with embodiments of the invention. Although many other internal components of the computer are not shown, those of ordinary skill in the art will appreciate that such components and the interconnections are well known. Accordingly, additional details concerning the internal construction of the computer need not be disclosed in connection with the present invention.

Those skilled in the art will appreciate that the invention may be practiced with various computer system configurations, including hand-held wireless devices such as mobile phones or PDAs, multiprocessor systems, microprocessor-based or programmable consumer electronics, minicomputers, mainframe computers, and the like. Any type of mobile device, such as for example iPads, tablets, iPhones, Android devices or Blackberries may be utilized in connection with embodiments of the invention. The invention may also be practiced in distributed computing environments where tasks are performed by remote processing devices that are linked through a communications network. In a distributed computing environment, program modules may be located in both local and remote computer storage media including memory storage devices.

Those skilled in the art will further appreciate that, in one embodiment of the invention, the user may utilize the interface as described above, without connection to a network (such as the Internet). Such a computing environment may include a processing unit, a user input interface, a system memory and a memory interface. In this embodiment, a user device, such as a laptop computer or tablet device may be compatible with a program or other software that is loaded onto the user device and stored in the user device memory. This allows the user to access the diagnostic inquiry functionality and/or other related functionalities as described in the present application (for instance, allowing the user to query and/or input information, assigning weight or value to the user's queries and/or responses in order to assess and diagnose a patient, suggesting 'best practice' recommendations for testing, treatment and noting approval with any applicable regulations), and to further allow those functionalities to be implemented by a processor, without requiring connection to a network. The user may subsequently access the software via an interface in order to input a query or information as described, for example, in FIG. 5.

Although the aforementioned components are shown as discrete modules, each of the modules may alternatively be integrated with one another. If the modules are discrete, multiple modules may operate cooperatively as will be further explained below.

Figure 5:
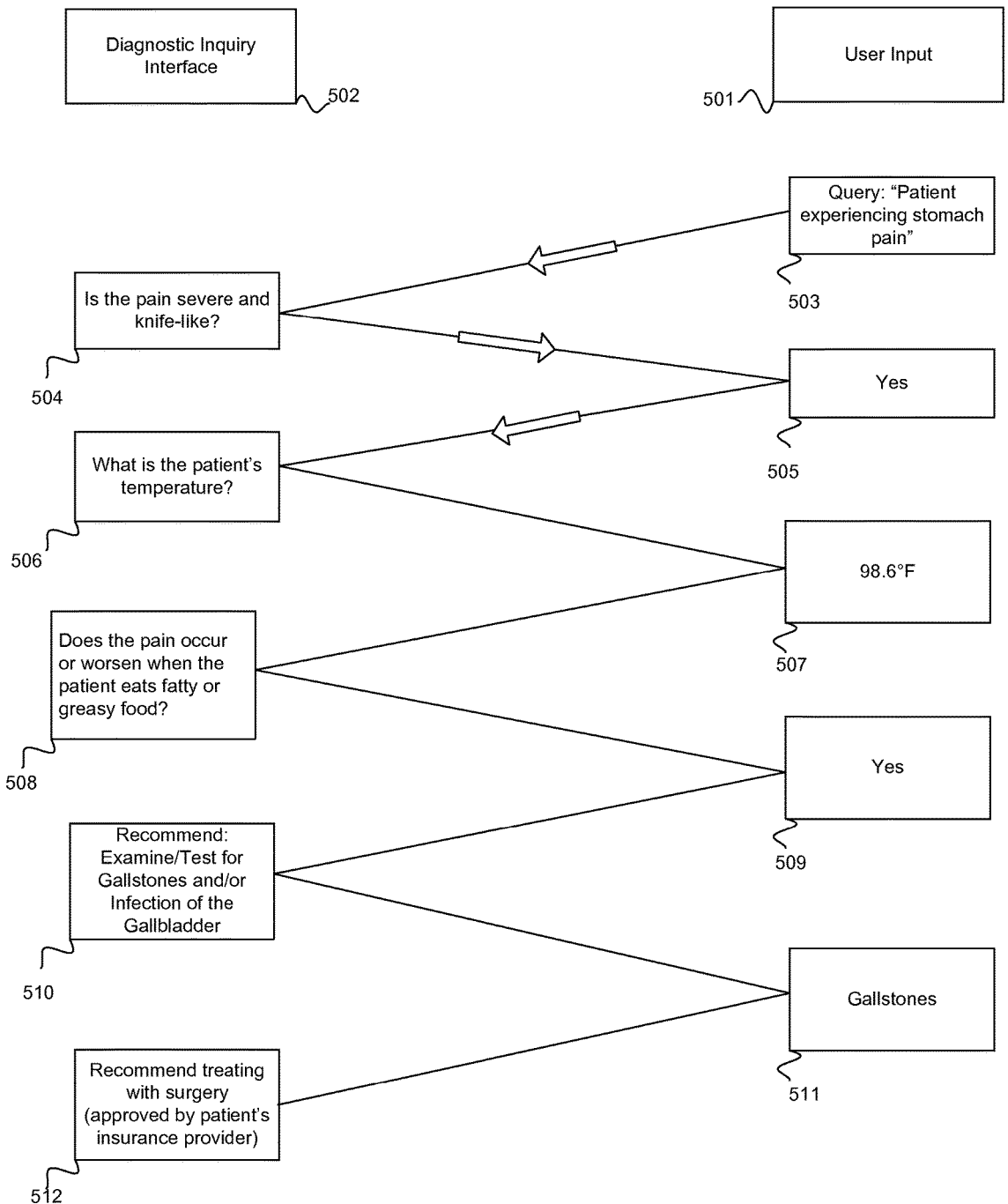
FIG. 5 illustrates user input into a device displaying a user interface in accordance with an embodiment of the invention.

Referring to FIG. 5, the possible user responses and input 501 to a diagnostic inquiry interface 502 are shown. It should be noted that the progression depicted in FIG. 5 is intended to be only one example of how user input 501 may direct the output of the diagnostic inquiry interface 502, and is not intended to be limiting in any way. At first the diagnostic inquiry interface 502 might show a screen with a text box that requires the user to enter a keyword or a specific query 503. For instance, the user may enter the phrase "patient experiencing stomach pain." Based on this query, the diagnostic inquiry interface 502 will present questions according to the user's responses. For instance, in response to the user's affirmation that the pain is "severe and knife-like" at 505, the diagnostic inquiry may attempt to ascertain whether the patient has a fever at 506, in order to rule out possible conditions (e.g., appendicitis). Had the user responded that the pain was not "severe and knife-like," this diagnosis may have been ruled out right away and the inquiry could be re-focused based on another possible diagnosis. After inputting the patient's normal temperature is normal at 507, the diagnostic inquiry interface 502 may assign a value or weight to this information (e.g., an "8" on a 1-10 scale) and may further display two possible diagnoses at 510. The interface 502 may also include a screen or access to a screen with additional information on the possible diagnoses and/or more information on recommended examination procedures or specific tests that may be performed to confirm one of the diagnoses. In one embodiment, the user may subsequently (e.g., once test results have been returned) select or enter the confirmed diagnosis 511. In a further embodiment, the interface 502 may display possible treatment options for the confirmed diagnosis 512. Additionally, at this time (or in some embodiments, in a separate step) the screen may also display whether these treatment options are approved and/or covered by, for example, regulations such as Medicare or Medicaid, hospital regulations, and insurance procedures.

What is claimed is:

1. A computer-implemented interactive system operating in cooperation with a health care institution on behalf of at least one user, the system comprising:
   at least one processor and at least one storage medium adapted to implement the following:
      interactive processing components for processing information to provide collaborative interaction over a network between the at least one user, at least one primary database, and at least one secondary database associated with a third party, the collaborative interaction including deployment of:
         a search module in response to a query associated with a user device;
         a diagnostic inquiry module comprising an interactive sequence of at least two linked inquiries transmitted to the user device, wherein the interactive sequence comprises at least a first query and a second query, the second query being based on a response to the first query;
         a record processing system associated with the diagnostic inquiry module, the record processing system being operable to associate a response to each query in the interactive sequence with patient record information stored in the at least one primary database; and
         a recording module capable of automatically accessing and updating the patient record information during a recurring appointment associated with the at least one user, and
      user interface tools associated with the user device for accepting input from the diagnostic inquiry module, including an alphabetical, numerical, or alphanumerical scheduling code referring to scheduling an opening and closing of the patient record by at least one other user, and correspondingly displaying output as determined by the interactive processing components, wherein the output comprises a list of potential differential diagnoses displayed by a history diagnosis module in order of descending likelihood of diagnosis, the history diagnosis module suggesting a format of treatment, and the user interface tools being further operable to display and allow the at least one user to respond to the interactive sequence of the at least two linked inquiries;
   wherein an acuity is assigned to at least one diagnosis of the potential differential diagnoses based on a co-morbidity associated with the at least one diagnosis, the acuity being displayed to the at least one user.

2. The system of claim 1, wherein the user device is at least one of a smartphone, a tablet device, and a laptop computer.

3. The system of claim 1, wherein the history diagnosis module is operable to transmit to the at least one user, in connection with the at least one primary database, at least one possible diagnosis in response to the diagnostic inquiry module.

4. The system of claim 3, wherein the history diagnosis module is further operable to transmit to the at least one user, subsequent medical guidance related to treatment of the at least one possible diagnosis.

5. The system of claim 4, wherein the at least one secondary database guides the transmission of the history diagnosis module to indicate whether the subsequent medical guidance is allowed by applicable rules stored within the secondary database.

6. The system of claim 1, wherein the patient record information is also transmitted to the user device over the network.

7. The system of claim 1, wherein the diagnostic inquiry module is operable to assign a weight to the user responses to the interactive sequence of the at least two linked inquiries.

8. A computer-implemented interactive method for diagnosing a patient operated in cooperation with a health care institution on behalf of at least one user, the method comprising:
processing stored information and user input to provide collaborative interaction between the at least one user and at least one database, the collaborative interaction comprising a search module responsive to a query associated with a user device;
deploying a diagnostic inquiry module associated with the at least one database via a network, the diagnostic inquiry module further comprising an interactive sequence of at least two linked inquiries transmitted to the user device, wherein the interactive sequence comprises at least a first query and a second query, the second query being based on a response to the first query;
accepting the user input from the diagnostic inquiry module, the user input including an alphabetical, numerical, or alphanumerical scheduling code referring to scheduling an opening and closing of a patient record by at least one other user, and correspondingly displaying output on the user device as determined by a processor and interactive processing components, wherein the output comprises a list of potential differential diagnoses displayed by a history diagnosis module in order of descending likelihood of diagnosis, the history diagnosis module suggesting a format of treatment; and,
displaying an interface on a user device, the interface operable to allow the at least one user to respond to the interactive sequence of the at least two linked inquiries;
wherein an acuity is assigned to at least one diagnosis of the potential differential diagnoses based on a co-morbidity associated with the at least one diagnosis, the acuity being displayed to the at least one user.

9. The method of claim 8, further comprising transmitting, via the history diagnosis module, at least one possible diagnosis in response to the diagnosis inquiry module.

10. The method of claim 9, further comprising transmitting, to the at least one user, subsequent medical guidance related to treatment of the at least one possible diagnosis.

11. The method of claim 10, further comprising displaying, by the interface, at least one indication that the subsequent medical guidance is allowed by applicable rules within a rules database.

12. The method of claim 11, wherein the applicable rules comprise at least one government regulation restricting at least one procedure in the format of treatment.

13. The method of claim 11, further comprising:
displaying, by the interface, at least one further indication that the subsequent medical guidance is not allowed by applicable rules within a rules database;
providing an override function for the at least one user to prescribe the subsequent medical guidance; and
requesting approval from an insurance representative for the subsequent medical guidance.

14. The method of claim 11, wherein the subsequent medical guidance comprises at least one surgical procedure; and further comprising:
prompting audibly at least one clinician performing the at least one surgical procedure; and
receiving at least one verbal description from the at least one clinician while performing the at least one surgical procedure.

15. The method of claim 8, further comprising accessing, by the diagnostic inquiry module, at least one patient record within a record processing system, the record processing system associating the diagnosis inquiry module with the patient record stored in a patient database.

16. The method of claim 15, further comprising transmitting the patient record to the user device.

17. The method of claim 8, further comprising assigning a weight to the user responses to the interactive sequence of the at least two linked inquiries.

18. The method of claim 8, wherein the acuity assignment determines a remuneration schedule for the at least one user.

19. The method of claim 8, wherein the history diagnosis module is further operable to:
direct a physical examination of a patient based on responses to the interactive sequence; and
direct testing of the patient based on the list of potential differential diagnoses.

20. A computer-implemented interactive system for use in diagnosing a patient, the system comprising:
a user device associated with a preloaded module that includes at least one database associated with a catalogue of medical symptoms and conditions;
at least one processor and at least one non-transitory storage medium adapted to implement the following components:
interactive processing components for processing information to provide collaborative interaction between a user and the at least one database, the collaborative interaction including deployment of:
a search module in response to a query associated with the user device; and
a diagnostic inquiry module comprising an interactive sequence of at least two linked inquiries transmitted to the user device;
wherein the interactive sequence comprises at least a first query and a second query, the second query being based on a response to the first query; and,
user interface tools associated with the user device for accepting input from the diagnostic inquiry module, the user input including an alphabetical, numerical, or alphanumerical scheduling code referring to scheduling an opening and closing of a patient record by at least one other user, and correspondingly displaying output as determined by the interactive processing components, wherein the output comprises a list of potential differential diagnoses displayed by a history diagnosis module in order of descending likelihood of diagnosis, the history diagnosis module suggesting a format of treatment, and wherein the user interface tools are operable to display and allow the user to respond to the interactive sequence of the at least two linked inquiries as user responses to the interactive sequence;

wherein an acuity is assigned to at least one diagnosis of the potential differential diagnoses based on a co-morbidity associated with the at least one diagnosis, the acuity being displayed to the at least one user.

21. The system of claim 20, wherein the diagnostic inquiry module is operable to assign a weight to the user responses to the interactive sequence of the at least two linked inquiries.

\* \* \* \* \*